(12) United States Patent
Schnur

(10) Patent No.: US 6,335,344 B1
(45) Date of Patent: Jan. 1, 2002

(54) PHENYLAMINO-SUBSTITUTED TRICYCLIC DERIVATIVES FOR TREATMENT OF HYPERPROLIFERATIVE DISEASES

(75) Inventor: Rodney C. Schnur, deceased, late of Mystic, CT (US), by Wendy W. Schnur, executrix

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/202,738

(22) PCT Filed: Nov. 6, 1997

(86) PCT No.: PCT/IB97/00675

§ 371 Date: Sep. 29, 1999

§ 102(e) Date: Sep. 29, 1999

(87) PCT Pub. No.: WO97/49688

PCT Pub. Date: Dec. 31, 1997

Related U.S. Application Data

(60) Provisional application No. 60/020,491, filed on Jun. 24, 1996.

(51) Int. Cl.[7] ................ C07D 239/70; A61K 31/519
(52) U.S. Cl. ................ 514/267; 544/250; 544/251
(58) Field of Search .................. 544/250, 251; 514/267

(56) References Cited

FOREIGN PATENT DOCUMENTS

WO          95/19970          *  7/1999

OTHER PUBLICATIONS

Burke et al. Protein–tyrosine kinases: potential targets for anticancer drug development, Stem Cell, 12:1–6, Jan. 1994.*

* cited by examiner

*Primary Examiner*—Mukund J. Shah
*Assistant Examiner*—Hong Liu
(74) *Attorney, Agent, or Firm*—Peter C. Richardson; Paul H. Ginsburg; Jeffrey N. Myers

(57) ABSTRACT

The present invention relates to compounds of the formula (I)

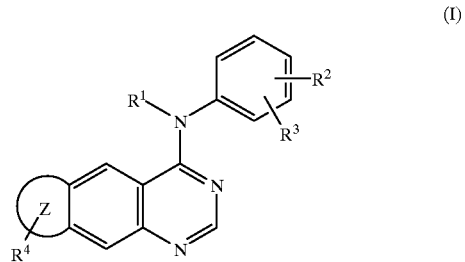

and to pharmaceutically acceptable salts thereof, wherein $R^1$–$R^4$ and Z are as defined herein. The compounds of formula (I) are useful as antiproliferative agents. The invention further relates to pharmaceutical compositions and methods of treating hyperproliferative disorders such as cancer, using such compounds.

5 Claims, No Drawings

PHENYLAMINO-SUBSTITUTED TRICYCLIC DERIVATIVES FOR TREATMENT OF HYPERPROLIFERATIVE DISEASES

This application claims the benefit of U.S. Provisional Application No. 60/020,491, filed Jun. 24, 1996.

BACKGROUND OF THE INVENTION

This invention relates to phenylamino-substituted tricyclic derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

It is known that a cell may become cancerous by virtue of the transformation of a portion of its DNA into an oncogene (i.e. a gene that upon activation leads to the formation of malignant tumor cells). Many oncogenes encode proteins which are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate specific tyrosine residues in proteins and hence to influence cell proliferation. It is known that such kinases are often aberrantly expressed in common human cancers such as breast cancer, gastrointestinal cancer such as colon, rectal or stomach cancer, leukemia, and ovarian, bronchial or pancreatic cancer. It has also been shown that epidermal growth factor receptor (EGFR), which possesses tyrosine kinase activity, is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease, and may reduce successful blastocyte implantation and therefore be useful as a contraceptive. See PCT international application publication number WO 95/19970 (published Jul. 27, 1995).

SUMMARY OF THE INVENTION

The present invention relates to compounds of the formula

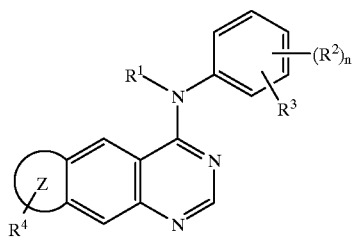

and to pharmaceutically acceptable salts thereof, wherein:

n is 0 to 2;

$R^1$ is hydrogen or $C_1-C_6$ alkyl optionally substituted by 1 to 3 substituents independently selected from the group consisting of halo, $C_1-C_4$ alkoxy, —$NR^6R^7$, and —$SO_2R^5$;

each $R^2$ is independently selected from the group consisting of halo, hydroxy, $C_1-C_6$ alkyl, —$NR^6R^7$, and $C_1-C_4$ alkoxy, wherein said alkyl group and the alkyl moieties of said $R^2$ groups are optionally substituted by 1 to 3 substituents independently selected from the group consisting of halo, $C_1-C_4$ alkoxy, —$NR^6R^7$, and —$SO_2R^5$;

$R^3$ is azido or -(ethynyl)-$R^8$ wherein $R^8$ is hydrogen or $C_1-C_6$ alkyl optionally substituted by hydroxy, —$OR^6$, or —$NR^6R^7$;

$R^4$ is H, $C_1-C_4$ alkyl, $(C_1-C_4$ alkoxy)$C_1-C_4$ alkyl, $C_1-C_4$ alkanoyl, $C_1-C_4$ alkoxy or —$S(O)_x(C_1-C_4$ alkyl) wherein x is 0 to 2, and wherein said alkyl group and the alkyl moieties of said $R^4$ groups are optionally substituted by 1 to 3 halogens;

each $R^5$ is $C_1-C_4$ alkyl optionally substituted by 1 to 3 halogens;

$R^6$ and $R^7$ are independently selected from hydrogen and $R^5$; and,

Z is a 5 to 8 membered fused ring that includes 0 to 3 heteroatoms selected from O, S and N.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties.

The term "alkoxy", as used herein, unless otherwise indicated, includes O-alkyl groups wherein "alkyl" is defined above.

The term "alkanoyl", as used herein, unless otherwise indicated, includes —C(O)-alkyl groups wherein "alkyl" is defined above.

In the present invention, the Z moiety of formula I represents a 5 to 8 membered used ring that includes 0 to 3 heteroatoms selected from O, S and N. The Z moiety includes saturated and unsaturated fused rings, and aromatic and non-aromatic fused rings.

Preferred compounds of formula I include those wherein $R^3$ is -(ethynyl)-$R^8$.

Other preferred compounds of formula I include those wherein Z is selected from

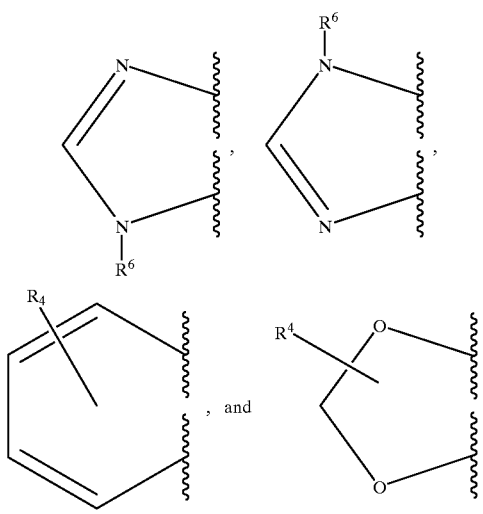

Other preferred compounds of formula I include those wherein Z is selected from the group of four moieties referred to above and $R^4$ is H or $C_1$–$C_4$ alkyl, $R^1$ is H, and n is 0.

Other preferred compounds of formula I include those wherein $R^3$ is -(ethynyl)-$R^8$ and $R^8$ is H.

Other preferred compounds of formula I include compounds of the formula

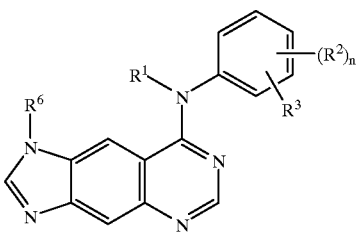

II wherein $R^1$, $R^2$, $R^3$, $R^6$ and n are as defined above.

Preferred compounds of formula II include those wherein n is 0, $R^1$ is H, $R^3$ is -(ethynyl)-$R^8$, and $R^6$ is H or methyl. Particularly preferred compounds of formula II include those wherein $R^8$ is H.

Specific preferred compounds of formula I include the following 4-(3-ethynylanilino)-imidazo[4,5-g]quinazoline;
(3-ethynyl-phenyl)-(3-methyl-3H-imidazo[4,5-g] quinazolin-8-yl)-amine;
(3-ethynyl-phenyl)-(1-methyl-1H-imidazo[4,5-g] quinazolin-8-yl)-amine;
benzo[g]quinazolin-4-yl-(3-ethynyl-phenyl)-amine;
[1,3]dioxolo[4,5-g]quinazolin-8-yl-(3-ethynyl-phenyl)-amine; and, pharmaceutically acceptable salts of the foregoing compounds.

The invention also relates to a pharmaceutical composition for the treatment of a hyperproliferative disorder in a mammal which comprises a therapeutically effective amount of a compound of formula I, or a pharmaceutically acceptable salt thereof, and a pharmaceutically acceptable carrier.

In a preferred embodiment, the pharmaceutical composition is for the treatment of cancer such as brain, lung, squamous cell, bladder, gastric, pancreatic, breast, head, neck, prostate, colorectal, oesophageal, gynecological or thyroid cancer.

In another preferred embodiment, the pharmaceutical composition is for the treatment of a non-cancerous hyperproliferative disorder such as psoriasis or benign hyperplasia of the skin or prostate.

The invention also relates to a pharmaceutical composition for the treatment of pancreatitis or kidney disease in a mammal which comprises a therapeutically effective amount of a compound of formula I, or a pharmaceutically acceptable salt thereof, and a pharmaceutically acceptable carrier.

The invention also relates to a pharmaceutical composition for the prevention of blastocyte implantation in a mammal which comprises a therapeutically effective amount of a compound of formula I, or a pharmaceutically acceptable salt thereof, and a pharmaceutically acceptable carrier.

The invention also relates to a method of treating a hyperproliferative disorder in a mammal which comprises administering to said mammal a therapeutically effective amount of the compound of formula I or a pharmaceutically acceptable salt thereof.

In a preferred embodiment, the method relates to the treatment of cancer such as brain, lung, squamous cell, bladder, gastric, pancreatic, breast, head, neck, oesophageal, prostate, colorectal, gynecological or thyroid cancer.

In another preferred embodiment the method relates to the treatment of a non-cancerous hyperproliferative disorder such as psoriasis or benign hyperplasia of the skin or prostate.

The invention also relates to a method of treating pancreatitis or kidney disease in a mammal which comprises administering to said mammal a therapeutically effective amount of the compound of formula I or a pharmaceutically acceptable salt thereof.

The invention also relates to a method of blastocyte formation in a mammal which comprises administering to said mammal a therapeutically effective amount of the compound of formula I or a pharmaceutically acceptable salt thereof.

The phrase "pharmaceutically acceptable salt(s)", as used herein, unless otherwise indicated, includes salts of acidic or basic groups which may be present in the compounds of formulas I and II.

Certain compounds of formulas I and II may have asymmetric centers and therefore exist in different enantiomeric forms. This invention relates to the use of all optical isomers and stereoisomers of the compounds of formulas I and II and mixtures thereof. The compounds of formulas I and II may also exist as tautomers. This invention relates to the use of all such tautomers and mixtures thereof.

DETAILED DESCRIPTION OF THE INVENTION

In general, the compounds of formula I can be prepared according to one or more synthetic methods that are disclosed in PCT international application number PCT/US95/00911 (publication number WO 95/19970, published Jul. 27, 1995) (hereafter "WO 95/19970"), which is incorporated herein by reference in its entirety. The following reaction Schemes 1 and 2 illustrate the preparation of the compounds

SCHEME 1

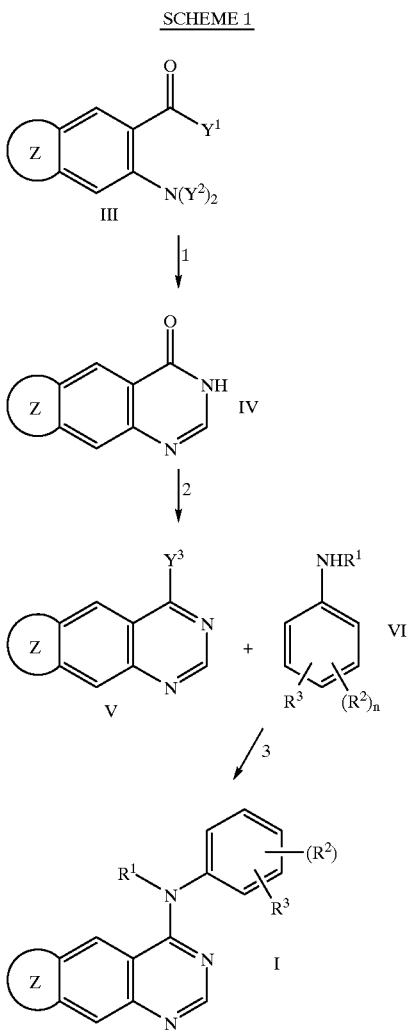

SCHEME 2

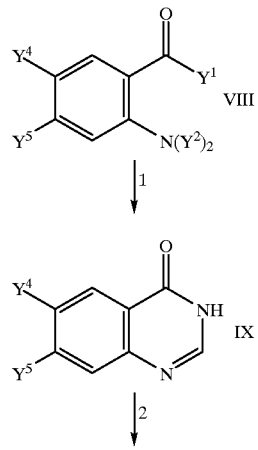

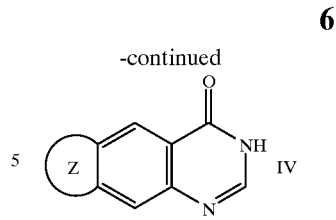

Scheme 1 provides a general illustration of the preparation of the compounds of formula I. Substituents $R^2$, $R^3$ and $R^4$ can be introduced into the compound of formula I at any suitable point in the synthesis of the compounds of formula I. As illustrated in Scheme 1, substituents R2 and R3 are included in intermediate VI prior to coupling with intermediate V, but these substituents can be included after the coupling reaction if necessary. Synthetic methods of introducing substituents $R^2$, $R^3$ and $R^4$ into the compound of formula I or the intermediates referred to above will be apparent to those skilled in the art.

With reference to Scheme 1, the compound of formula III can be obtained commercially or prepared according to methods known to those skilled in the art. Where $Y^1$ is hydroxy and $Y^2$ is H, the tricyclic compound of formula IV is prepared by condensation of the compound of formula III with formamide. This reaction is done through the addition of the compound of formula III to formamide under nitrogen at a temperature of 120–150° C. for 30 minutes to 1.5 hours, followed by heating the mixture to a temperature of 170–180° C. for 1 to 3 hours to provide the tricyclic compound of formula IV. Where $Y^1$ is —$NH_2$ and $Y^2$ is O, the compound of formula III is hydrogenated over 5% palladium on carbon under a pressure of about 60 psi for about 1 hour to reduce the nitro group to an amino group. The resulting compound is then dissolved in triethyl orthoformate and heated to reflux for about 18 hours to provide the tricyclic compound of formula IV.

In step 2 of Scheme 1, the compound of formula IV is converted to the compound of formula V in which $Y^3$ is either methylthio or chloro. To prepare the compound of formula V in which $Y^3$ is chloro, the compound of formula IV, and optionally phosphorus pentachloride, is added to phosphorus oxychloride and heated to reflux under nitrogen for about 2 to 4 hours to provide the compound of formula V in which $Y^3$ is chloro. In the alternative, this chlorination reaction can be done by adding the compound of formula IV and styrene-bound triphenylphosphine to dichloroethane and carbon tetrachloride and heating the mixture to reflux for 30 minutes to 2 hours to provide the compound of formula V in which $Y^3$ is chloro. To prepare the compound of formula V in which $Y^3$ is methylthio, the oxo moiety of the compound of formula IV is converted to a thio moiety by heating a mixture of the compound of formula IV and $P_2S_5$ in pyridine to reflux for 14 to 18 hours. The resulting compound and KOH in aqueous MeOH is treated with MeI at ambient temperature (20–25° C.) for 30 minutes to 4 hours to provide the compound of formula V in which $Y^3$ is methylthio.

In step 3 of Scheme 1, the $Y^3$ group of the compound of formula V is displaced by the aniline compound of formula VI to provide the biaryl amine of formula I. In this process, the compound of formula V and the aniline of formula VI in a solvent, such as isopropanol or t-butanol, are heated to reflux for about 2 to 10 hours to provide the compound of formula I. The $R^4$ substituent can be introduced into the Z moiety of the compound of formula I according to synthetic methods known to those skilled in the art.

Scheme 2 illustrates preparing the quinazoline portion of the tricyclic ring structure before the addition of the Z moiety, followed by cyclization of the Z moiety on to the quinazoline ring. Steps 1 and 2 of Scheme 2 can be done as a single step depending on the type of tricyclic ring structure that is being prepared. The compound of formula IV that is prepared according to Scheme 2 is converted to the compound of formula VII in the manner described in steps 2 and 3 of Scheme 1 above.

Scheme 2 can be illustrated with reference to the preparation of 4-oxo-3H-oxazolo[5,4-g]quinazoline. In this process, 5-hydroxy-2,4-dinitrobenzamide (compound of formula VIII in which $Y^1$ is amino, $Y^2$ is O, $Y^4$ is hydroxy and $Y^5$ is nitro) is hydrogenated over 5% palladium over carbon at about 60 psi for about 3 hours to give 2,4-diamino-5-hydroxybenzamide. To this product is added formic acid and the mixture is heated to reflux for about 48 hours to provide 4-oxo-3H-oxazolo[5,4-g]quinazoline. In this process, steps 1 and 2 of Scheme 2 are performed as a single step.

Other tricyclic compounds of formula IV are similarly prepared according to one or more synthetic methods disclosed in WO 95/19970, referred to above, in which the general synthetic steps of Scheme 2 are employed. For example, 4-oxo-3H-pyrrolo[3,2-g]quinazoline can be prepared according to the process described in Example 3 in WO 95/19970. 4-Oxo-3H-oxazolo[5,4-g]quinazoline can be prepared according to the process described in Example 5 in WO 95/19970. 4-Oxo-3H-triazolo[4,5-g]quinazoline can be prepared according to the process described in Example 7 in WO 95/19970. 6,N-Methyl-3H-imidazo[4,5-g]quinazolin-4-one can be prepared according to the process described in Example 9 in WO 95/19970. Methods to prepare other compounds of formula IV will be apparent to those skilled in the art.

Suitable pharmaceutically-acceptable salt of the compounds of the present invention include acid-addition salts of said compounds which are prepared from inorganic or organic acids such as hydrochloric, hydrobromic, sulphuric, phosphoric, methanesulfonic, benzenesulfonic, trifluoroacetic, citric, lactic and maleic acid. Such salts can be prepared by conventional methods. For example, they can be prepared simply by contacting the acidic and basic entities, usually in a stoichiometric ratio, in either an aqueous, non-aqueous or partially aqueous medium, as appropriate. The salts are recovered by filtration; by precipitation with a non-solvent, preferably an etheral or hydrocarbon solvent, followed by filtration and by evaporation of a solvent, or, in the case of aqueous solutions, by lyophilization.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of the present invention are potent inhibitors of the erbB family of oncogenic and protooncogenic protein tyrosine kinases such as epidermal growth factor receptor (EGFR), erbB2, HER3, or HER4 and thus are all adapted to therapeutic use as antiproliferative agents (e.g., anticancer agents) in mammals, particularly humans. In particular, the compounds of this invention are therapeutants or prophylactics for the treatment of a variety of human tumors (including renal, liver, kidney, bladder, breast, gastric, ovarian, colorectal, prostate, pancreatic, lung, vulval, thyroid, hepatic carcinomas, sarcomas, glioblastomas, and various head and neck tumors), and other hyperplastic conditions such as benign hyperplasia of the skin (e.g., psoriasis) or prostate (e.g., BPH). In addition, it is expected that a quinazoline of the present invention may possess activity against a range of leukemias and lymphoid malignancies.

The active compounds may also be expected to be useful in the treatment of additional disorders in which aberrant expression ligand/receptor interactions, activation or signalling events related to various protein tyrosine kinases, whose activity is inhibited by the compounds of the present invention, are involved.

Such disorders may include those of neuronal, glial, astrocytal, hypothalamic, and other glandular, macrophagal, epithelial, stromal, and blastocoelic nature in which aberrant function, expression, activation or signalling of the erbB tyrosine kinases may be involved. In addition, the compounds of the present invention may have therapeutic utility in inflammatory, angiogenic and immunologic disorders involving both identified and as yet unidentified tyrosine kinases that are inhibited by the compounds of the present invention.

The in vitro activity of the active compounds in inhibiting the receptor tyrosine kinase (and thus subsequent proliferative response, e.g., cancer) may be determined by the procedure detailed below.

Activity of the active compounds, in vitro, can be determined by the amount of inhibition of the phosphorylation of an exogenous substrate (e.g., $Lys_3$-Gastrin or polyGluTyr (4:1) random copolymer (I. Posner et. al., J. Biol. Chem. 267 (29), 20638–47 (1992)) on tyrosine by epidermal growth factor receptor kinase by a test compound relative to a control. Affinity purified, soluble human EGF receptor (96 ng) is obtained according to the procedure in G. N. Gill, W. Weber, Methods in Enzymology 146, 82–88 (1987) from A431 cells (American Type Culture Collection, Rockville, Md.) and preincubated in a microfuge tube with EGF (2 μg/ml) in phosphorylation buffer+vanadate (PBV: 50 mM HEPES, pH 7.4; 125 mM NaCl; 24 mM $MgCl_2$; 100 μM sodium ortho vanadate), in a total volume of 10 μl, for 20–30 minutes at room temperature. The test compound, dissolved in dimethylsulfoxide (DMSO), is diluted in PBV, and 10 μl is mixed with the EGF receptor/EGF mix, and incubated for 10–30 minutes at 30° C. The phosphorylation reaction is initiated by addition of 20 μl $^{33}$P-ATP/substrate mix (120 μM $Lys_3$-Gastrin (sequence in single letter code for amino acids, KKKGPWLEEEEEAYGWLDF), 50 mM Hepes pH 7.4, 40 μM ATP, 2 μCi γ-[$^{33}$P]-ATP) to the EGFr/EGF mix and incubated for 20 minutes at room temperature. The reaction is stopped by addition of 10 μl stop solution (0.5 M EDTA, pH 8; 2 mM ATP) and 6 μl 2N HCl. The tubes are centrifuged at 14,000 RPM, 40° C., for 10 minutes. 35 μl of supernatant from each tube is pipetted onto a 2.5 cm circle of Whatman P81 paper, bulk washed four times in 5% acetic acid, 1 liter per wash, and then air dried. This results in the binding of substrate to the paper with loss of free ATP on washing. The [$^{33}$P] incorporated is measured by liquid scintillation counting. Incorporation in the absence of substrate (e.g., $lys_3$-gastrin) is subtracted from all values as a background and percent inhibition is calculated relative to controls without test compound present.

Such assays, carried out with a range of doses of test compounds, allow the determination of an approximate $IC_{50}$ value for the in vitro inhibition of EGFR kinase activity. Although the inhibitory properties of the compounds of Formula I vary with structural change as expected, the activity generally exhibited by these agents, determined in the manner described above, is in the range of $IC_{50}$= 0.0001–30 μM.

Activity of the active compounds, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", Cancer Res., 35, 2434–2439 (1975) and Corbett, T. H., et al., "A Mouse Colon-tumor Model for Experimental Therapy", Cancer Chemother. Rep. (Part 2)", 5, 169–186 (1975), with slight modifications. Tumors are induced in the left flank by s.c. injection of $1 \times 10^6$ log phase cultured tumor cells (human MDA-MB-468 breast or human HN5 head and neck carcinoma cells) suspended in 0.10 ml RPMI 1640. After sufficient time has elapsed for the tumors to become palpable (2–3 mm in diameter) the test animals (athymic mice) are treated with active compound (formulated by dissolution in DMSO typically at a concentration of 50 to 100 mg/mL followed by 1:9 dilution into saline or, alternatively, 1:9 dilution into 0.1% Pluronic P105 in 0.9% saline) by the intraperitoneal (ip) or oral (po) routes of administration twice daily (i.e., every 12 hours) for 5 consecutive days. In order to determine an anti-tumor effect, the tumor is measured in millimeters with Vernier calipers across two diameters and the tumor size (mg) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, Cancer Chemother. Rep., 3, 1–104 (1972). Results are expressed as percent inhibition, according to the formula: Inhibition (%)=$(TuW_{control} - TuW_{test})/TuW_{control} \times$ 100%. The flank site of tumor implantation provides reproducible dose/response effects for a variety of chemotherapeutic agents, and the method of measurement (tumor diameter) is a reliable method for assessing tumor growth rates.

Administration of the active compounds can be effected by any method which enables delivery of the compounds to the site of action (e.g., cancer cells). These methods include oral routes, rectal routes, intraduodenal routes, parenteral injection (including intravenous, subcutaneous, intramuscular, intravascular or infusion), topical administration, etc.

The amount of active compound administered will, of course, be dependent on the subject being treated, on the severity of the affliction, on the manner of administration and on the judgement of the prescribing physician. However an effective dosage is in the range of approximately 0.001–100 mg/kg, preferably 1 to 35 mg/kg in single or divided doses. For an average 70 kg human, this would amount to 0.05 to 7 g/day, preferably 0.2 to 2.5 g/day. The foregoing dosages can be followed for the treatment of hyperproliferative diseases, kidney disease, pancreatitis or the prevention of blastocyte formation (to effect contraception).

The composition may, for example, be in a form suitable for oral administration such as a tablet, capsule, pill, powder, sustained release formulation, solution, or suspension; for parenteral injection such as a sterile solution, suspension or emulsion; or for topical administration such as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the present invention as an active ingredient. In addition, it may include other medicinal or pharmaceutical agents, carriers, adjuvants, etc.

Pharmaceutical compositions according to the invention may contain 0.1%–95% of the active compound, preferably 1%–70%. In any event, the composition or formulation to be administered will contain a quantity of active compound in an amount effective to alleviate or reduce the signs in the subject being treated, i.e., hyperproliferative diseases, over the course of the treatment.

Exemplary parenteral administration forms include solutions or suspensions of active compounds in sterile aqueous solutions, for example aqueous propylene glycol or dextrose solutions. Such dosage forms can be suitably buffered, if desired.

Suitable pharmaceutical carriers include inert diluents or fillers, water and various organic solvents. The pharmaceutical compositions may, it desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefor, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences., Mack Publishing Company, Easter, Pa., 15th Edition (1975).

The therapeutic compounds may also be administered to a mammal other than a human. The dosage to be administered to a mammal will depend on the animal species and the disease or disorder being treated. The therapeutic compounds may be administered to animals in the form of a capsule, bolus, tablet or liquid drench. The therapeutic compounds may also be administered to animals by injection or as an implant. Such formulations are prepared in a conventional manner in accordance with standard veterinary practice. As an alternative the therapeutic compounds may be administered with the animal feedstuff and for this purpose a concentrated feed additive or premix may be prepared for mixing with the normal animal feed.

The hyperproliferative disease treatment described above may be applied as a sole therapy or may involve, in addition to the active compound, one or more other antitumor substances. Such conjoint treatment may be achieved by way of the simultaneous, sequential, cyclic or separate dosing of the individual components of the treatment.

The following examples illustrate the preparation of the compounds of the invention. High pressure liquid chromatography (HPLC) used in the following examples and preparations was effected according to the following method unless modified in specific examples. Perkin-Elmer Pecosphere® 3×3 C. cartridge column (3 mm×3 cm, C18; available from Perkin Elmer Corp., Norwalk, Conn. 06859) with a Brownlee (trademark) RP-8 Newguard precolumn (7 micron, 3.2 mm×15 mm, available from Applied Biosystems Inc. San Jose, Calif. 95134) which was previously equilibrated in pH 4.50, 200 mM ammonium acetate buffer. Samples were eluted using a linear gradient of 0–100% acetonitrile/pH4.50, 200 mM $NH_4$ acetate over 10 minutes with a flow rate of 3.0 mL/min. Chromatograms were generated over the range 240–400 nm using a diode array detector.

It should be understood that the invention is not limited to the particular embodiments shown and described herein, but that various changes and modifications may be made without departing from the scope of the invention as defined by the claims.

EXAMPLE 1

4-(3-Ethynylanilino)-imidazo[4,5-g]quinazoline hydrochloride

A mixture of 4-methylthio-6H-imidazo[4,5-g]quinazoline (0.0455 g, 0.210 mmol), prepared as described in Leonard, N. J.; Morrice, A. G.; Sprecker, M. A., *J. Org. Chem.*, 1975, 40 (3), 356–363, 3-ethynylaniline (0.0672 g, 0.574 mmol) and pyridine hydrochloride (0.0274 g, 0.237 mmol) in t-butanol (5 mL) was heated to reflux for 6 hours then cooled to room temperature. Precipitate was collected and washed with t-butanol to give 4-(3-ethynylanilino)-imidazo[4,5-g]-quinazoline hydrochloride as a yellow solid: 0.0349 g (58%); $^1$H NMR (DMSO-$d_6$) δ4.34 (1H, s), 7.48 (1H, m), 7.53 (1H, m), 7.82 (1H, m), 7.98 (1H, s), 8.13 (1H, s), 8.81 (1H, s), 8.99 (1H, s), 9.24 (1H, s), 11.49 (1H, br s); m/e 286 (M+1).

EXAMPLE 2

(3-Ethynyl-phenyl)-(3-methyl-3H-imidazo[4,5-g] guinazolin-8-yl)-amine hydrochloride A mixture of 8-N-methyl-4-methylthioimidazo[4,5-g] quinazoline (0.0505 g, 0.219 mmol), 3-ethynylaniline (0.0670 g, 0.572 mmol) and pyridine hydrochloride (0.0325 g, 0.281 mmol) in t-butanol (2 mL) was refluxed for 4 hours then cooled to ambient temperature (20–25°). Precipitate was collected and refluxed for 20 minutes in ethyl acetate, then filtered off to yield (3-ethynyl-phenyl)-(3-methyl-3H-imidazo[4,5-g]quinazolin-8-yl)-amine hydrochloride as a yellow solid: 0.0445 g (60%); mp 226.5–228.8° C. (decomposed); m/e 300 (M+1).

EXAMPLE 3

(3-Ethynyl-phenyl)-(1-methyl-1H-imidazo[4.5-g] guinazolin-8-yl)-amine hydrochloride A mixture of 6-N-methyl-4-methylthioimidazo[4,5-g] quinazoline (0.1016 g, 0.441 mmol), 3-ethynylaniline (0.1683 g, 1.44 mmol), and pyridine hydrochloride (0.0769 g, 0.665 mmol) in t-butanol (3 mL) was refluxed for 4 hours and cooled to ambient temperature. (3-Ethynyl-phenyl)-(1-methyl-1H-imidazo[4,5-g]quinazolin-8-yl)-amine hydrochloride precipitated from the reaction mixture: 0.0981 g (66%); mp 233–238° C. (decomposed).

EXAMPLE 4

Benzo[g]guinazolin-4-yl-(3-ethynyl-phenyl)-amine hydrochloride

A mixture of 3-amino-2-naphthoic acid (5.16 g, 27.6 mmol) and formamide (7 mL, 193 mmol) was heated to 125° C. for 1 hour, then to 175° C. for 90 minutes. The reaction mixture was cooled and 3H-Benzo[g]quinazolin-4-one was recovered as yellow solid by filtration: 3.37 g (62%); $^1$H NMR (DMSO-$d_6$) δ7.57–7.72 (2H, m), 8.08–8.16 (2H, m), 8.22 (1H, d, J=11 Hz), 8.27 (1H, s), 8.86 (1H, s).

A mixture of 3H-benzo[g]quinazolin-4-one (1.00 g, 5.07 mmol) and styrene-bound triphenylphosphine (2.53 g (approx. 3 mmoles/g), 7.61 mmol) in 15 mL dichloroethane and 15 mL carbon tetrachloride was heated to reflux for 1 hour, cooled to ambient temperature (20–25° C.) and filtered. Solvents were removed in vacuo to give 4-Chlorobenzo[g]quinazoline: 0.3881 g (36%); $^1$H NMR (DMSO-$d_6$) δ7.63–7.71 (2H,m), 8.10 (1H, d, J=10 Hz), 8.28 (1H, d, J=10 Hz), 8.32 (1H, s), 8.69 (1H, s), 8.82 (1H, s).

A mixture of 4-chloro-benzo[g]quinazoline (0.1017 g, 0.474 mmol) and 3-ethynylaniline (0.1685 g, 1.44 mmol) in 5 mL t-butanol was refluxed for 3 hours then cooled to ambient temperature. Benzo[g]quinazolin-4-yl-(3-ethynyl-phenyl)-amine hydrochloride was collected and recrystallized from 40 mL ethanol: 0.0916 g (58%); mp 231–234° C. (decomposed).

EXAMPLE 5

[1,3]Dioxolo[4,5-g]quinazolin-8-yl-(3-ethynylphenyl)-amine

A mixture of 3,4-(methylenedioxy)-6-nitrobenzaldehyde (25 g, 128 mmol) and potassium permanganate (40 g, 253 mmol) in a mixture of 300 mL water and 200 mL acetone was stirred overnight at ambient temperature and then heated to 100° C. for 1 hour. The reaction mixture was filtered through Celite®, acetone was removed in vacuo, and the product precipitated from the water solution by acidification to pH 1.2 with concentrated hydrochloric acid to give 6-nitro-benzo[1,3]dioxole-5-carboxylic acid [19.88 g (73%)].

6-nitro-benzo[1,3]dioxole-5-carboxylic acid (19 g, 90 mmol) in 500 mL ethanol was hydrogenated at 50 psig over 5 g of 5% palladium on carbon for 2 hours. Catalyst was filtered off with Celite® and solvent was removed in vacuo to give 6-amino-benzo[1,3]dioxole-5-carboxylic acid; 4.5 g (27%) used without further purification.

A mixture of 6-amino-benzo[1,3]dioxole-5-carboxylic acid (4.3 g, 23.7 mmol) and formamide (15 mL) was heated to 140° C. for 2 hours, then to 170° C. for 2 hours. After cooling to room temperature, precipitate was collected to give 7H-[1,3]dioxolo[4,5-g]quinazolin-8-one (1.11 g, 27%).

A mixture of 7H-[1,3]dioxolo[4,5-g]quinazolin-8-one (0.550 g, 2.78 mmol) and phosphorus pentachloride (0.800 g, 3.84 mmol) in 3 mL phosphorus oxychloride was heated to a gentle reflux for 2.5 hours. Solvent was removed in vacuo, and azeotroped with toluene. Residue was dissolved in ethyl acetate and washed with 5% sodium bicarbonate solution and then filtered, and then solvent was removed in vacuo to give 8-chloro-[1,3]dioxolo[4,5-g]quinazoline (0.400 g, 74%).

A mixture of 8-chloro-[1,3]dioxolo[4,5-g]quinazoline (0.200 g, 1.04 mmol) and 3-ethynylaniline (0.127 g, 1.09 mmol) in 5 mL isopropanol was heated to reflux overnight, then cooled to ambient temperature. Precipitate was collected and washed to give [1,3]dioxolo[4,5-g]quinazolin-8-yl-(3-ethynyl-phenyl)-amine (0.266 g, 78%): mp greater than 350° C.

What is claimed is:

1. A compound of the formula

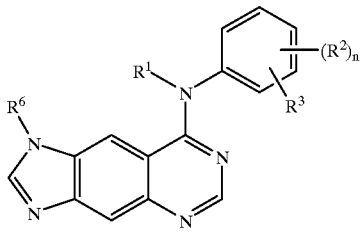

(I)

or a pharmaceutically acceptable salt thereof, wherein:

n is 0 to 2;

$R^1$ is hydrogen or $C_1$–$C_8$ alkyl optionally substituted by 1 to 3 substituents independently selected from the group consisting of halo, $C_1$–$C_4$ alkoxy, —$NR^6R^7$, and —$SO_2R^5$;

each $R^2$ is independently selected from the group consisting of halo, hydroxy, $C_1$–$C_6$ alkyl, —$NR^6R^7$, and $C_1$–$C_4$ alkoxy, wherein said alkyl group and the alkyl moieties of said $R^2$ groups are optionally substituted by 1 to 3 substituents independently selected from the group consisting of halo, $C_1$–$C_4$ alkoxy —$NR^6R^7$ and —$SO_2R^5$;

$R^3$ is -(ethynyl)-$R^8$, wherein $R^8$ is hydrogen or $C_1$–$C_6$ alkyl optionally substituted by hydroxy, —$OR^6$, or —$NR^6R^7$;

each $R^5$ is $C_1$–$C_4$ alkyl optionally substituted by 1 to 3 halogens; and $R^6$ and $R^7$ are independently selected from hydrogen and $R^5$.

2. The compound of claim 1 wherein n is 0, R1 is H, R3 is -(ethynyl)-R8, and R6 is H or methyl.

3. The compound of claim 2 wherein $R^8$ is H.

4. The compound of claim 1 wherein said compound is selected from the group consisting of:

4-(3-ethynylanilino)-imidazo[4,5g]quinazoline;
(3-ethynyl-phenyl)-(1-methyl-3H-imidazo[4,5g]quinazolin-8-yl)-amine; and pharmaceutically acceptable salts of the foregoing compounds.

5. A pharmaceutical composition which comprises a therapeutically effective amount of the compound of claim 1 and a pharmaceutically acceptable carrier.

* * * * *